United States Patent [19]

Shibasaki et al.

[11] Patent Number: 4,709,064

[45] Date of Patent: Nov. 24, 1987

[54] β-N-SUBSTITUTED AMINOTHIOL ESTER AND PROCESS FOR PREPARING THE SAME

[75] Inventors: Masakatsu Shibasaki, Mitaka; Takamasa Iimori, Sagamihara, both of Japan

[73] Assignee: Sagami Chemical Research Center, Tokyo, Japan

[21] Appl. No.: 887,296

[22] Filed: Jul. 23, 1986

[30] Foreign Application Priority Data

Jul. 24, 1985 [JP] Japan .................................. 60-162144
Jul. 24, 1985 [JP] Japan .................................. 60-162145

[51] Int. Cl.$^4$ ............................................. C07F 7/10
[52] U.S. Cl. .................................... 556/418; 540/200
[58] Field of Search ........................................ 556/418

[56] References Cited

U.S. PATENT DOCUMENTS 4,444,685  4/1984  Amato et al. ................... 556/418 X

OTHER PUBLICATIONS

J. Am. Chem. Soc., 1984, 106, 4819 to 4825.
Chemistry Letters, pp. 1927 to 1930, 1984.
Chemistry Letters, pp. 651 to 654, 1985.
Tetrahedron Letters, vol. 26, No. 7, pp. 937 to 940, 1985.
Tetrahedron Letters, vol. 26, No. 12, pp. 1523 to 1526, 1985.

*Primary Examiner*—Paul F. Shaver
*Attorney, Agent, or Firm*—Armstrong, Nikaido, Marmelstein & Kubovcik

[57] ABSTRACT

β-N-substituted aminothiol ester represented by the general formual (I):

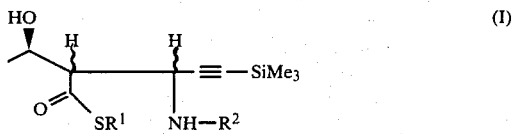

wherein $R^1$ is an alkyl group or an aryl group and $R^2$ is an aralkyl group, a process for preparing the same, and an azetidinone derivative represented by the general formula (VI):

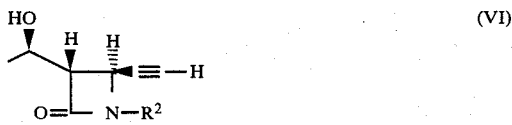

wherein $R^2$ is as above.

The β-N-substituted aminothiol ester (I) of the present invention can be an excellent intermediate for preparing the β-lactam (II).

2 Claims, No Drawings

β-N-SUBSTITUTED AMINOTHIOL ESTER AND PROCESS FOR PREPARING THE SAME

BACKGROUND OF THE INVENTION

The present invention relates to β-N-substituted aminothiol esters represented by the general formula (I):

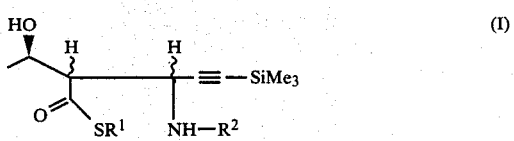

wherein $R^1$ is an alkyl group or an aryl group and $R^2$ is an aralkyl group, a process for preparing the same, and azetidinone derivative represented by the general formula (VI):

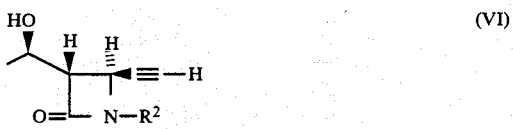

wherein $R^2$ is an aralkyl group.

β-N-Substituted aminothiol ester (I) of the present invention can be introduced into carbapenem β-lactam antibiotics such as thienamycin. The carbapenem β-lactam antibiotics show an excellent antibacterial activity against almost all bacteria including Pseudomonas aerugihosa, the antibacterial activity being much higher than the conventional drugs and with an excellent stability against β-lactamase. Accordingly, the carbapenem β-lactam antibiotics are greatly expected as the β-lactam antibiotics of fourth generation.

Hitherto, the carbapenum β-lactam antibiotics have been prepared by chemical synthesis in industry since its productivity in fermentation is quite low. In this point, the carbapenem β-lactam antibiotics are quite different from the conventional penicillins or cephalosporin antibiotics.

Various carbapenem β-lactam antibiotics have hitherto been in clinical stage. It is known by a person skilled in the art that these antibiotics are mainly prepared from an intermediate compound, i.e. β-lactam represented by the general formula (II):

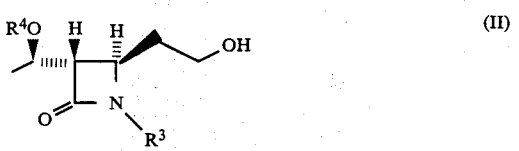

wherein $R^3$ and $R^4$ are a protective group.

As a process for preparing the β-lactam represented by the above formula (II), there have been known (1) a process in which a monocyclic β-lactam ring having a side chain at 4-position is formed by asymmetric synthesis with an optically active amino acid or an enzyme and then a side chain is introduced at 3-position, (2) a process in which asymmetric carbon atoms corresponding to 3-position, 4-position and 1'-position are selectively formed by a special means and then the β-lactam ring is formed, and (3) a process in which a monocyclic β-lactam having a side chain at 3-position is formed from L-threonine or optically active penicillins and then a side chain is introduced at α b-position [Masayuki Shibuya, "Yukigoseikagaku Kyokaishi, 41, 62(1983)].

However, the above process (1) is hard to be applied to an industrial process since it is rather difficult to introduce the side chain at 3-position and thus it is unsuitable for production in a large scale. Also the process (2), though the process has been industrially employed, has disadvantages such as a large number of preparing steps and involving the optical resolution. Further, the process (3), though the desired product can be obtained in an optically active form in the process, has also a disadvantage of so many producing steps. Recently, a process with a small number of synthesizing steps has been reported using optically active 3-hydroxybutyric acid [J. Am. Chem. Soc., 106, 4819 (1984); Chem. Lett., 1927 (1984); Chem. Lett., 651 (1985); Tet. Lett., 26, 937 (1985); Tet. Lett., 26, 1523 (1985)]. However, the process is still unsatisfactory in view point of a stereo-selectivity and a yield. As a result of earnest study of the present inventors in order to solve the above-mentioned problems, it has been found that β-N-substituted aminothiol ester represented by the above-mentioned general formula (I) can be an excellent intermediate for producing β-lactam compound represented by the above-mentioned general formula (II).

On the other hand, among compounds prepared starting from optically active 3-hydroxybutyric acid, one of the intermediate with broad appication is a compound represented by the formula (VII):

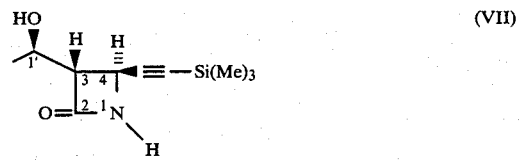

However, by the conventional method for the synthesis, the desired compound represented by the formula (VII) is produced as a by-product and the undesired stereoisomer represented by the formula (VIII):

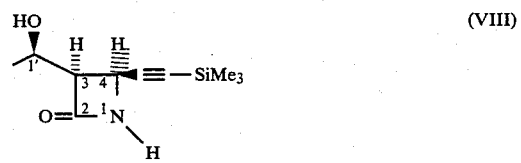

is produced with a high selectlvity. Therefore, for introducing into the carbapenem β-lactam antibiotics such as thienamycin, a much complicated process of epimerization at 3-position is required [J. Am. Chem. Soc., 106, 4816 (1984); Chem. Lett., 1927 (1984); Chem. Lett., 651 (1985)]. Further, a process for preparing the above compounds (VII) and (VIII) comprises aldol condensation between the compound represented by the general formulas (IX):

wherein R is methyl group or an alkyl group and the compound represented by the formula (X):

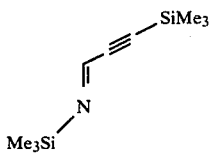 (X)

Also it is noted that, in the above reaction, trimethylsilyl group is indispensable as a protective group of nitrogen atom and the reaction does not proceed with the protective groups other than trimethylsilyl group.

The present inventors have found that the azetidinone derivatives represented by the general formula (VI) is produced with a high selectivity from the optically active hydroxybutyric acid via the compound (I). The intermediate of the β-lactam compound represented by the general formula (II) can be derived from the azetidinone derivatives represented by the general formula (VI) without a complicated process of epimerization at 3-position.

SUMMARY OF THE INVENTION

In accordance with the pesent invention, there is provided a β-N-substituted aminothiol ester represented by the general formula (I):

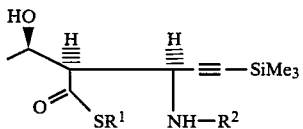 (I)

wherein $R^1$ is an alkyl group or an aryl group and $R^2$ is an arlkyl group. Also, in accordance with the present invention, there is provided a process for preparing a β-N-substituted aminothiol ester represented by the general formula (I), which comprises reacting a β-hydroxythiol ester represented by the general formula (III):

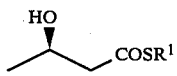 (III)

wherein $R^1$ is an alkyl group or an aryl group, with a borone compound represented by the general formula (IV):

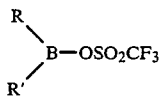 (IV)

wherein R and R' are an alkyl group or a cycloalkyl group, or R and R' are taken together to form a ring with borone atom, in the presence of a tertiary amine, and then reacting an imine represented by the general formula (V):

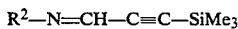 (V)

wherein $R^2$ is an aralkyl group, with the reaction mixture, followed by treatment with hydrogen peroxide. Further, in accordance with the present invention, there is provided an azetidinone derivative represented by the general formula (VI):

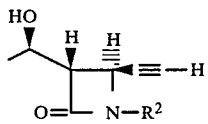 (VI)

wherein $R^2$ is an aralkyl group.

DETAILED DESCRIPTION

In the present invention, the β-N-substituted aminothiol ester represented by the general formula (I) is produced by (a) reacting a β-hydroxythiol ester represented by the general formula (III):

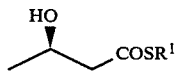 (III)

wherein $R^1$ is an alkyl group or an aryl group, with a borone compound represented by the general frmula (IV):

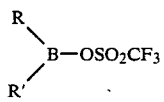 (IV)

wherein R and R' are an alkyl group or a cycloalkyl group, or R and R' are taken together to form a ring with borone atom, in the presence of a tertiary amine, (b) reacting an imine repesented by the general formula (V):

 (V)

wherein $R^2$ is an aralkyl group, with the obtained reaction mixture, and (c) treating the obtained product with hydrogen peroxide.

The β-hydroxytiol ester represented by the general formula (III) can be easily obtained by protecting hydroxyl group of β-hydroxycarboxylic acid, subjecting the resultant to condensation reaction by dehydration with the corresponding mercaptan, and removing the protective group (refer to Reference Examples). Examples of the β-hydroxythiol ester (III) are, for instance, S-phenyl-3(R)-hydroxybutanethioate, S-t-butyl-3(R)-hydroxybutane-thioate, S-ethyl-3-(R)-hydroxybutanethioate, S-sec-butyl-3(R)-hydroxybutanethioate, S-n-propyl-3(R)-hydroxybutane-thioate, S-isopropyl-3(R)-hydroxybutanethioate, and the like. On the other hand, the borone compound (IV) can be easily obtained industrially. Examples of the borone compound (IV) are, for instance, 9-borabicyclo[3.3.1]nonyltrifluoromethanesulfonate, dicyclopentyltrifluoromethanesulfonyloxyborane, di-n-butyltrifluoromethanesulfonyloxyborane, and the like.

It is necessary that the reaction between the β-hydroxythiol ester (III) and the borone compound (IV) is conducted in the presence of a tertiary amine. Examples of the tertiary amine are, for instance, diisopropylethylamine, triethylamine, trimethylamine, tributylamine, and the like. Diisopropylethylamine is preferably used for efficiently conducting the reaction. The reaction is carried out in a solvent. Examples of the solvent are, for instance, a halogenated hydrocarbon such as methylene chloride, chloroform or 1,2-dichloroethylene, an ether such as diethyl ether, tetrahydrofuran (THF) or dimethoxyethane (DME), an aromatic hydrocarbon such as toluene or xylene, and the like. The reaction proceeds smoothly at a temperature of from −78° C. to room temperature.

The thus obtained reaction mixture is reacted with the imine represented by the general formula (V). Examples of the imine (V) are, for instance, N-3-trimethylsilylpropynylidenebenzylamine, N-3-trimethylsilylpropynylidene-p-methoxyanisidine, N-3-trimethylsilylpropynylidene-o-methoxyanisidine, N-3-trimethylsilylpropynylidene-p-methoxybenzylamine, and the like. Solvent used in the reaction with the imine may be the same solvents as used in the reaction between the β-hydroxythiol ester (III) and the borone compound (IV). The reaction proceeds easily at a temperature of from −78° C. to room temperature.

After reaction with the imine (V), the obtained product is treated with hydrogen peroxide to give the β-N-substituted aminothiol ester represented by the general formula (I). Hydrogen peroxide is usually used as an about 30% aqueous solution. The amount of hydrogen peroxide ranges from 1 to 50 equivalent based on the β-hydroxythiol ester. The reaction solution is preferably cooled to a temperature of from −25° C. to room temperature when treated with hydrogen peroxide.

In the present invention, the azetidinone derivatives represented by the above-mentioned general formula (VI) can be prepared by hydrolyzing the thiol ester portion of the β-N-substituted aminothiol ester represented by the general formula (I):

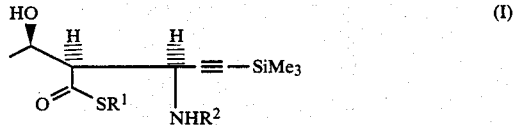

wherein R¹ is an alkyl group or an aryl group and R² is an aralkyl group, followed by heating under reflux in acetonitrile in the presence of triphenylphosphine and 4,4'-dipyridyldisulfide.

The β-N-substituted aminothiol ester represented by the general formula (I) of the present invention can be converted into the optically active β-lactam represented by the general formula (II) in a small number of steps and with high yield by forming the β-lactam ring to give the compound represented by the general formula (VI), protecting the hydroxyl group, partially reducing the triple bond and carrying out the hydroboration reaction. Accordingly, the β-N-substituted aminothiol ester (I) of the present invention can be an excellent intermediate for preparing the β-lactam (II).

The present invention is more specifically described and explained by means of the following Reference Examples and Examples. It is to be understood that the present invention is not limited to such Examples and various changes and modifications may be made in the invention without departing from the spirit and scope thereof.

REFERENCE EXAMPLE 1

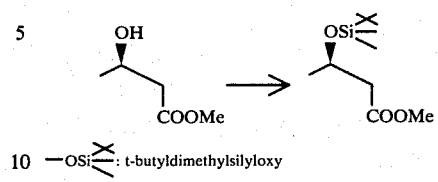

−OSi≡: t-butyldimethylsilyloxy

There were dissolved 5.91 g (50 mmol) of methyl 3-hydroxybutyrate and 3.74 g (55 mmol) of imidazole in 20 ml of DMF, to which 8.29 g (55 mmol) of t-butyldimethylsilylchloride was added by several portions.

After stirring the mixture for 30 minutes at room temperature, ice-water was added and extraction with diethyl ether was conducted three times. The extract was washed with a saturated aqueous solution of sodium chloride and dried with anhydrous magnesium sulfate, followed by concentration under reduced pressure. The obtained concentrated solution was distilled at 62° to 68° C. under a pressure of 5 mmHg to give 10.51 g of methyl (−)-3-t-butyldimethylsilyloxybutyrate.

Yield: 91%

Thin layer chromatography: 0.4 (hexane:diethyl ether=20:1)

Infrared absorption spectrum: (neat) 1735 cm$^{-1}$

Nuclear magnetic resonance spectrum: δ0.03, 0.06 (each 3H;s), 0.85(9H;s), 1.20(3H;d J=5), 2.42 (2H; m), 3.75(3H; s) and 4.25(1H; m)

Mass spectrum: 115, 133, 159 [M-(Me+COOMe)], 175[M-Bu]and 217[M-Me]

$[\alpha]_D^{20}$ −31.75° (c=1.94, CHCl3)

REFERENCE EXAMPLE 2

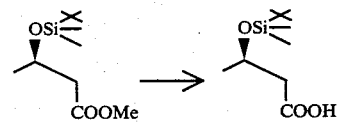

There was dissolved 3.58 g (15.4 mmol) of methyl (−)-3-t-butyldimethylsilyloxybutyrate in 30 ml of methanol, to which 30 ml of 1 N potassium hydroxide was added and the mixture was stirred for 15 minutes. After distilling away most methanol from the mixture, the solution was acidified with 1 N hydrochloric acid and extracted with diethyl ether. The extract was washed with a saturated aqueous solution of sodium chloride and dried with anhydrous magnesium sulfate, which was concentrated under reduced pressue to give 3.18 g of (−)-3-t-butyldimethylsilyloxybutyric acid.

Yield: 95%

Thin layer chromatography: 0.2 (hexane:diethyl ether=20:1)

Infrared absorption spectrum: (neat) 1710 cm$^{-1}$

Nuclear magnetic resonance spectrum: δ0.09(6H;s), 0.88(9H;s), 1.20(3H;d J=6), 2.46(2H;d J=6), and 4.27 (1H;dt J=6.6)

Mass spectrum: 110, 137, 197 and 218[M]

$[\alpha]_D^{20}$ −12.50° (C=0.96, CHCl3)

REFERENCE EXAMPLE 3

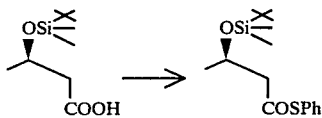

There were dissolved 3.18 g (19.2 mmol) of (−)-3-t-butyldimethylsilyloxybutyric acid and 2.26 ml (22 mmol) of thiophenol in 100 ml of methylene chloride, to which 4.53 g (22 mmol) of N,N'-dicyclohexylcarbodiimide was added. After stirring at room temperature for 2 hours, the mixture was filtered and the filtrate was concentrated and distilled at 110° to 116° C. under a pressure of 0.3 mmHg to give 5.00 g of (−)-3-t-butyl-dimethylsilyloxybutyric acid phenylthioester.

Yield: 83%

Thin layer chromatography: 0.3 (hexane:diethyl ether=20:1)

Infrared absorption spectrum: (neat) 1710 cm$^{-1}$

Nuclear magnetic resonance spectrum: $\delta$0.07(6H;s), 0.91(9H;s), 1.22(3H;d J=5), 2.61, 2.87(each 1H;dd J=15,7), 4.34(1H,m) and 7.41(5H;s)

Mass spectrum: 115, 159 [M-(Me+COSPh)], 253[M-Bu]and 295[M-Me]

$[\alpha]_D^{20}$−65.91° (c=0.98, CHC;3)

REFERENCE EXAMPLE 4

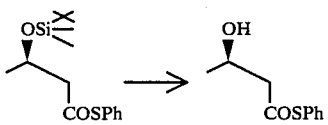

There was added 50 ml of a mixture of acetic acid, THF and water (3:1:1) to 3.26 g (10.4 mml) of (−)-3-t-butyldimethylsilyloxybutyric acid phenylthioester and the mixture was stirred at 50° C. for 24 hours. The obtained reaction mixture was concentrated and distilled at 128° to 130° C. under a pressure of 0.8 mmHg to give 1.91 g of (−)-3-hydroxybutyric acid phenylthioester.

Yield: 94%

Thin layer chromatography: 0.35 (hexane:diethyl ether=1:1)

Infrared absorption spectrum: (neat) 3440 and 1705 cm$^{-1}$

Nuclear magnetic resonance spectrum: $\delta$1.20(3H;d J=6), 2.82(2H;d J=6), 3.0(1H;br s), 4.22(1H;m) and 7.36 (5H;s)

Mass spectrum: 110[PhSH], 137[COSPh] and 196[M][$\alpha$]$_D^{20}$−42.25° (c=1.42, CHCl$_3$)

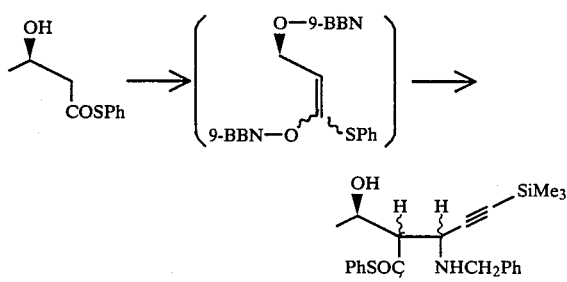

A mixture of 1.51 g (12.0 mmol) of 3-trimethysilyl-2-propynal and 1.31 ml (12.0 mmol) of benzylamine was stirred in 10 ml of diethyl ether for 30 minutes and the solvent was distilled away from the raction mixture under reduced pressure. The residue was distilled under reduced pressure of 1 mmHg in an oil bath at 120° to 130° C. to give an imine. The obtained imine was immediately used in the following reaction. There was dissolved 1.963 g (10.0 mmol) of (−)-3-hydroxybutyric acid phenylthioester in 40 ml of methylene chloride, to which 4.00 ml (23.0 mmol) of diisopropylethylamine and 5.94 g (22.0 mmol) of 9-BBN were added at −78° C. The mixture was heated to −25° C. for 1 hour and was stirred at −30° to −20° C. for 1 hour, to which 40 ml of a methylene chloride solution of the previously obtained imine was added dropwise for about 20 minutes at −30° to −20° C. The mixture was heated to room temperature for 1.5 hours and was stirred for 1 hour. After cooling the reaction mixture to −35° to −40° C., a mixture of 60 ml of a phosphate buffer (pH 7.0), 60 ml of methanol and 30 ml of 31% aqueous solution of hydrogen peroxide was added to the reaction mixture for about 20 minutes. The mixture was heated to 0° C. for 30 minutes, vigorously stirred at room temperature for 1 hour, and extracted twice with methylene chloride. The obtained extract was washed with a saturated solution of sodium chloride, dried with anhydrous sodium sulfate and then concentrated under reduced pressue. The concentrated solution was purified by silica-gel column-chromatography (C-300, eluent; hexane:diethyl ether=3:2) to give 2.054 g of 3-benzylamino-2-(1-hydroxyethyl)-5-trimethylsilyl-4-pentinic acid phenylthioester.

Yield: 50%

Thin layer chromatography: 0.41 (hexane:diethyl ether=3:2)

Infrared absorption spectrum: (neat) 3400, 2160, and 1700 cm$^{-1}$

Nuclear magnetic resonance spectrum: $\delta$0.23(9H;s), 1.25(3H;d J=7), 2.92(1H;t J=6), 3.6 to 3.8(2H; m), 4.03(1H;d J=12), 4.3(1H;m), 7.30(5H;s) and 7.39(5H;s)

Mass spectrum: 151, 216, 302 [M+−SPh]and 412 [M++1]

EXAMPLE 2

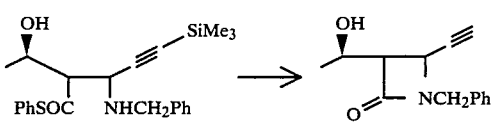

There was dissolved 2.054 g (5.0 mmol) of 3-benzylamino-2-(1-hydroxyethyl)-5-trimethylsilyl-4-pentinic acid phenylthioester in 40 ml of THF, to which 3 ml of 4 N potassium hydroxide was added and the mixture was stirred at room temperature for 3 hours. The reaction mixture was neutralized with 2 N hydrochloric acid and was extracted six times with ethyl acetate while conducting salting-out. The extract was dried with anhydrous magnesium sulfate and concentrated. There was added 250 ml of acetonitrile to the concentrated solution, and then 1.57 g (60 mmol) of triphenylphosphine was added, to which 1.32 g (6.0 mmol) of 2,2'-dipyridyldisulfide in 50 ml of acetonitrile was added dropwise for 40 minutes while vigorously stirring with heating under reflux. After the solution was further heated under reflux for 1 hour, the obtained reaction mixture was concentrated, followed by purification with 50 g of silica-gel column-chromatography (eluent;

methylene chloride→diethyl ether) and then with 50 g of silica-gel column-chromatography (eluent;hexane:-diethyl ether=1:4) to give 801 mg of a trans-form and 62 mg of a cis-form of 1-benzyl-4-ethynyl-3-(1-hydroxyethyl)-2-azetidinone.

As a sample of the trans-form for analysis, there was employed a trans-form obtained by recrystallizing the above obtained trans-form with diethyl ether.

Trans-form

Thin layer chromatography: 0.75 (diethyl ether)
Melting point: 134° C.
Infrared absorption spectrum: (CHCl3) 3450 and 1745 cm$^{-1}$
Nuclear magnetic resonance spectrum: δ1.24(3H;d J=6), 2.42(1H;d J=1), 2.7(1H;br s), 3.28(1H;dd J=5, 2.5), 4.1(3H;m), 4.73(1H;d J=15) and 7.29(5H;s)
Mass spectrum: 132, 186, 211 and 229 [M+]
Elementary analysis for $C_{14}H^{15}O_2N$: Calcd. (%):C 73.34, H 6.59, N 6.11. Found (%):C 73.45, H 6.54, N 6.10. $[\alpha]_D^{20}$ −20.45° (c=1.00, CHCl3)

Cis-form

Thin layer chromatography: 0.56 (diethyl ether)
Infrared absorption spectrum: (CHCl3) 3500 and 1750 cm$^{-1}$
Nuclear magnetic resonance spectrum: δ1.36(3H;d J=6), 2.68(1H;d J=2), 2.7(1H;br s), 3.27(1H;dd J=5,6),
Mass spectrum 150, 187, 205 and 229 [M+]
$[\alpha]_D^{20}$ −58.82° (c=1.22, CHCl3)

EXAMPLE 3

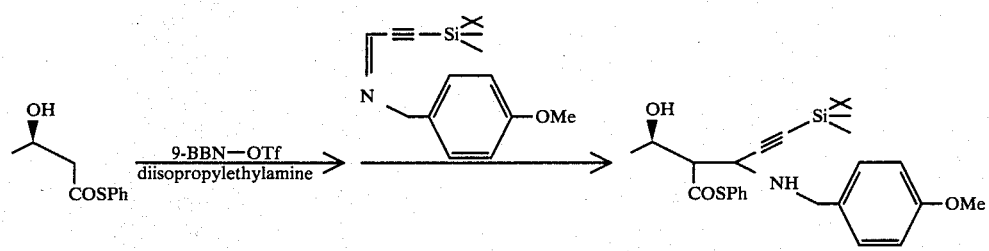

There were added 242 mg (1.9 mmol) of aldehyde and 263 mg (1.9 mmol) of methoxybenzylamine to 5 ml of ether and the mixture was stirred for 30 minutes. Then water was removed from the reaction mixture by azeotropic distillation with benzene. The obtained imine was used as it is in the following reaction. 290 mg of thioester dried enough was dissolved in 6 ml of methylene chloride, to which 0.6 ml (3.4 mmol) of diisopropylethylamine and then 0.92 g (3.4 mmol) of 9-BBN-OTf were added at −78° C. After stirring for 15 minutes at −78° C., the mixture was heated to −30° C. for 15 to 20 minutes and stirred at −25° to −20° C. for 2 hours. The solution was then cooled to −60° to −50° C. and thereto 5.6 ml of a methylene chloride solution of the previously prepared imine was added. After stirring at −60° to −50° C. for 10 to 20 minutes, the mixture was heated to −30° to −20° C. and stirred at −30° to −20° C. for 2 hours. The mixture was again cooled to −70° to −60° C. and thereto a mixture of 10 ml of phosphate buffer (pH 7.0), 5 ml of methanol and 5 ml of 31% aqueous solution of hydrogen peroxide was added dropwise. The mixture was then heated to room temperature, stirred at room temperature for 10 to 20 minutes and extracted three times with methylene chloride. The obtained extract was washed twice with a saturated aqueous solution of sodium chloride, dried with anhydrous sodium sulfate and concentrated under reduced pressure. The obtained residue was purified by silica-gel column-chromatography (WG 300, eluent; hexane:ether=3:1) to give 449 mg of a desired additive (yield: 68.8%).

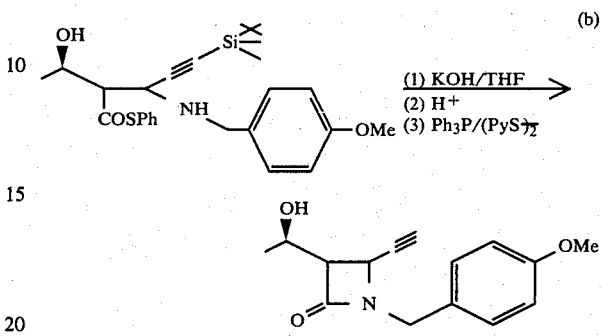

There was added 383 mg (0.87 mmol) of the obtained additive with imine to 5 ml of THF, to which 2.5 ml of 1 N potassium hydroxide was added, and the mixture was stirred for 5 hours. The reaction mixture was then neutralized with 1 N hydrochloric acid and extracted with ethyl acetate while conducting salting-out. The organic layer was dried with sodium sulfate and concentrated. The obtained concentrated solution was dissolved in 70 ml of acetonitrile, to which 287 mg (1.3 mmol) of dipyridyldisulide was added and then 10 ml of an acetonitrile solution of 342 mg (1.3 mmol) of triphenylphosphine was added dropwise to the mixture under reflux with heating. The mixture was further heated under reflux and concentrated, following by silica-gel column-chromatography (eluent; ether) to give 155 mg of a desired β-lactam (yield: 69%).

REFERENCE EXAMPLE 5

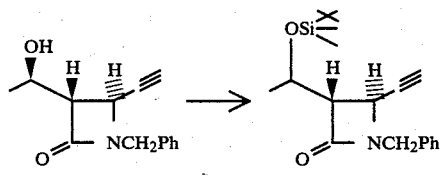

There was dissolved 206 mg (0.90 mmol) of 1-benzyl-4(S)-ethynyl-3(S)-[1(R)-hydroxyethyl]-2-azetidinone (trans-form) obtained in Example 2 in 3 ml of dimethylformamide, to which 180 mg (1.2 mmol) of a t-butyl-dimethylsilylchloride and 82 mg (1.2 mmol) of imidazole were added and the mixture was stirred at room temperature for a night. After diluting with diethyl ether, the reaction mixture was added with water and extracted three times with diethyl ether. The extract was washed with a saturated aqueous solution of sodium chloride, dried with anhydrous magnesium sulfate and concentrated. The residue was purified by 10 g of silica-gel column-chromatography (eluent; hexane:diethyl ether=2:1) to give 318 mg of 1-benzyl-4(S)-ethynyl-3(S)-[1(R)-t-butyldimethylsilyloxyethyl]-2-azethidinone.

Yield: quantitative

Thin layer chromatography: 0.4 (diethyl ether:hexane=1:2)

Infrared absorption spectrum: (CHCl$_3$) 1750 cm$^{-1}$

Nuclear magnetic resonance spectrum: δ0.06, 0.09 (each 3H;s), 0.86(9H;s), 1.24(3H;d J=6), 2.43 (1H;d J=2), 3.27(1H;dd J=3, 2.5), 4.2(3H;m), 4.70 (1H;d J=15) and 7.34(5H;s)

Mass spectrum: 242, 286 [M+—Bu] and 328 [M+—Me]

$[\alpha]_D^{20}$ −11.62° (c=1.00, CHCl$_3$)

REFERENCE EXAMPLE 6

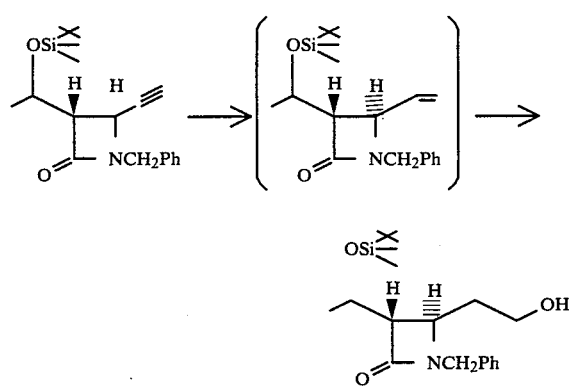

There were added 0.015 ml of quinoline and 1.5 ml of petroleum ether to 103 mg (0.30 mmol) of 1-benzyl-4(S)-ethynyl-3(S)-[1(R)-t-butyldimethysilyloxyethyl]-2-azetidinone, to which 1.5 mg of Lindlar catalyst was added. The mixture was vigorously stirred at room temperature for 12 hours under hydrogen atmosphere. The reaction solution was filtered and the filtrate was concentrated, to which 2 ml of petroleum ether and 3 mg of Lindlar catalyst were added and the reaction was continued for 36 hours under hydrogen atmosphere. The reaction solution was subjected to silica-gel (10 g) column-chromatography (eluent; benzene:methylene chloride=1:1) to give a partially reduced product including the starting material, which was employed in the following reaction without further purification. The partially reduced product including the starting material was dissolved in 2 ml of THF, to which 1.1 ml (0.63 mmol) of a THF solution of 9-BBN (0.6 M) was added while cooling with an ice bath. After the mixture was stirred in the ice bath for 1 hour, 0.5 ml (0.3 mmol) of a THF solution of 9-BBN (0.6 M) was added to the mixture and was stirred for 2 hours in the ice bath and then for 1 hour at room temperature. There were added 0.56 ml (2.3 mmol) of 4 N sodium hydroxide and 0.4 ml of 31% aqueous solution of hydroperoxide to the obtained reaction mixture on the ice bath and the resultant was stirred at room temperature for 1 hour. The reaction solution was diluted with diethyl ether, added with water and extracted three times with diethyl ether. The extract was washed with an aqueous solution of dilute sodium thiosulfate and then with a saturated aqueous solution of sodium chloride, dried with anhydrous magnesium sulfate and concentrated. The obtained residue was purified by 10 g of silica-gel column-chromatography (eluent; diethyl ether:hexane=3:1→5:1) to give 70 mg of 1-benzyl-3(S)-[1(R)-t-butyldimethylsilyloxyethyl]-4(R)-(2-hydroxyethyl)-2-azetidinone.

Yield: 64%

Thin layer chromatography: 0.3 (diethyl ether:hexane=3:1)

Infrared absorption spectrum: (CHCl$_3$) 3460 and 1740 cm$^{-1}$

Nuclear magnetic resonance spectrum: δ0.03, 0.07 (each 3H;s), 0.87(9H;s), 1.26(3H;d J=6), 1.8 (2H;m), 2.8(1H;br s), 3.02(1H;dd J=2, 8), 3.6 (3H;m), 4.2(2H;m), 4.61(1H;d J=15) and 7.3(5H;s)

Mass spectrum: 306 [M+—Bu] and 348 [M+—Me]

$[\alpha]_D^{20}$ −1.09° (c=1.20, CHCl$_3$)

REFERENCE EXAMPLE 7

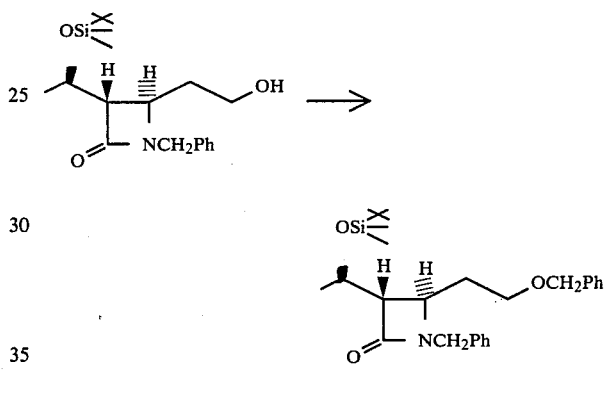

There were added 1 ml of THF and 0.6 ml of dimethylformamide to 13 mg (0.26 mmol) of sodium hydride (oiliness: 50%), to which 2 ml of a THF solution of 64 mg (0.18 mmol) of 1-benzyl-3(S)-[1(R)-t-butyldimethylsilyloxyethyl]-4(R)-(2-hydroxyethyl)-2-azetidinone on the ice bath and the mixture was stirred for 10 minutes. Thereto 0.03 ml (0.25 mmol) of benzyl bromide was added and the mixture was stirred at room temperature for a night. The reaction mixture was added with water, extracted three times with diethyl ether, and the obtained extract was washed with a saturated aqueous solution of sodium chloride, dried with anhydrous magnesium sulfate and concentrated. The obtained residue was purified by 10 g of silica gel-column chromatography (eluent; hexane:diethyl ether=1:1) to give 46 mg of 1-benzyl-4(R)-2-benzyloxyethyl)-3(S)-[1(R)-t-butyldimethylsilyloxyethyl]-2-azetidinone (yield: 58%).

The obtained compound completely corresponded to the compound described in the literature (T. Iimori and M. Shibasaki, Tetrahedron Lett., 26, 1523(1985)) and was efficiently converted into thienamycin.

What is claimed is:

1. β-N-Substituted aminothiol ester represented by the general formula (I):

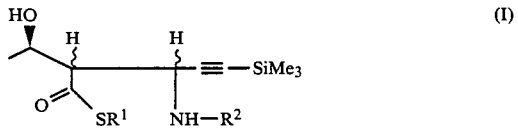

wherein $R^1$ is an alkyl group or an aryl group and $R^2$ is an aralkyl group.

2. A process for preparing β-N-substituted aminothiol ester represented by the general formula (I):

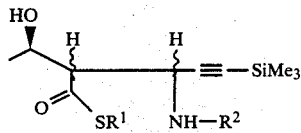 (I)

wherein $R^1$ is an alkyl group or an aryl group and $R^2$ is an aralkyl group, which comprises reacting β-hydroxythiol ester represented by the general formula (III):

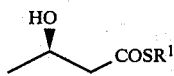 (III)

wherein $R^1$ is an alkyl group or an aryl group, with a borone compound represented by the general formula (IV):

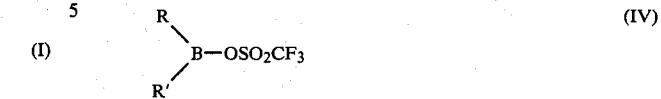 (IV)

wherein R and R' are an alkyl group or a cycloalkyl group, or R and R' are taken together to form a ring with borone atom, in the presence of a tertiary amine, and then reacting the obtained reaction mixture with an imine represented by the general formula (V):

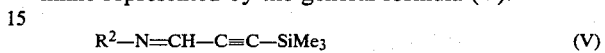 (V)

wherein $R^2$ is an aralkyl group, followed by treatment with hydrogen peroxide.

* * * * *